Jan. 12, 1954 H. C. SWIM Plant Pat. 1,241
ROSE PLANT
Filed Dec. 29, 1952
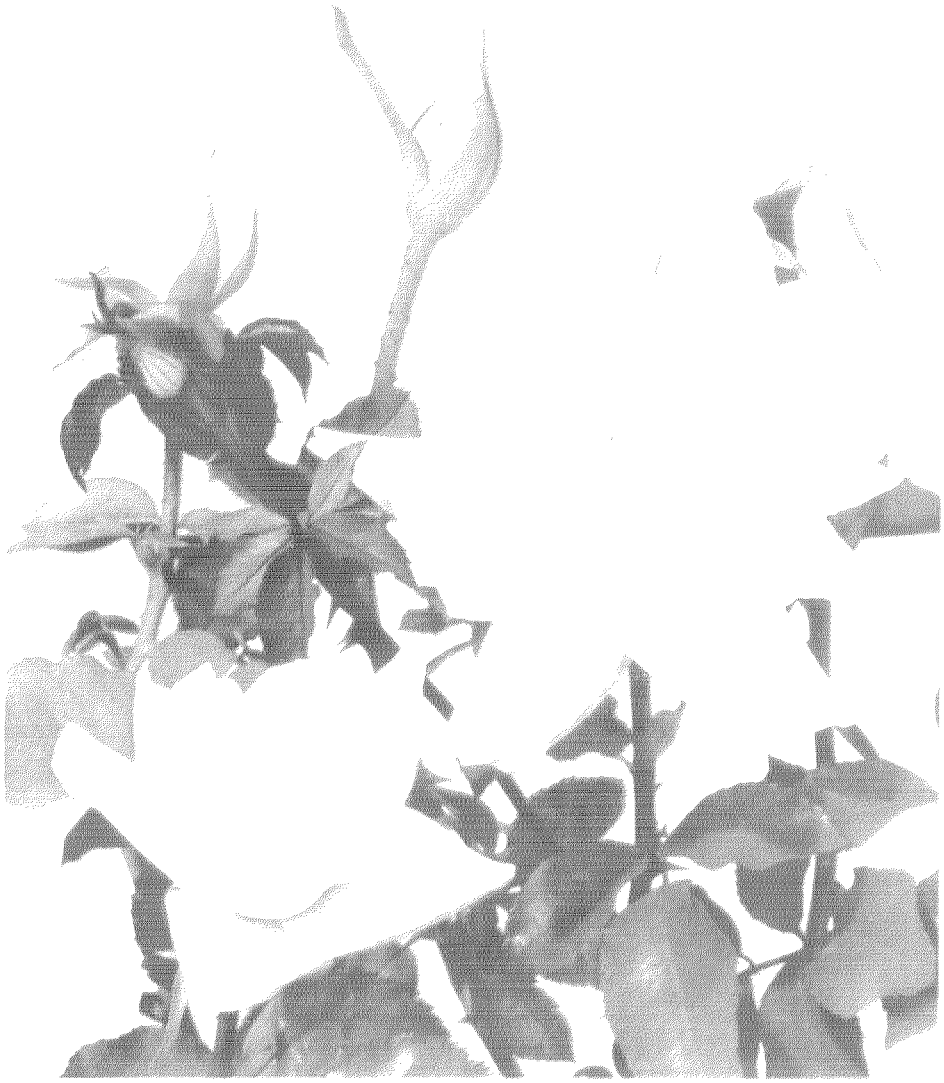
Inventor
H. C. Swim
By: Robert Cobb
Attorneys Patented Jan. 12, 1954 Plant Pat. 1,241

UNITED STATES PATENT OFFICE 1,241

ROSE PLANT

Herbert C. Swim, Ontario, Calif., assignor, by mesne assignments, to Arp Nursery Company, Tyler, Tex., a partnership consisting of Clark Kidd, Letcher A. Dean, and Letcher B. Dean, all of Tyler, Tex.

Application December 29, 1952, Serial No. 328,542

1 Claim. (Cl. 47—61)

The present invention relates to a new and distinct variety of rose plant of the hybrid tea class, which was originated by me by crossing the variety "Soeur Therese" (unpatented) with the variety "Golden Dawn" (unpatented).

The primary objection in making this cross was to produce a new variety of rose plant which combines the best characteristics of the two parent varieties. This objective was fully achieved, as evidenced by the following combination of outstanding characteristics in my new variety which distinguish it from its parents, as well as from all other varieties of its class.

(1) The bushy, compact, much-branched, slightly spreading habit of growth, inherited from the parent variety "Golden Dawn";

(2) The long-pointed and slightly urn-shaped form of the buds, inherited from the parent "Soeur Therese";

(3) The double petalage and superior petal substance, inherited from "Golden Dawn," with attendant lasting quality of the flowers which is typical of this parent variety;

(4) The rich yellow color of the flowers, which is a color that is normally quite fugitive in roses of this color class; and (5) The prolongation and retention of the richness of the flower coloring, with attendant long life of the flowers in respect to both color and form as the result of the substance inherited from "Golden Dawn."

My new variety differs in a marked degree from its seed parent "Soeur Therese" by the fact that the substance of the flowers of the new variety is substantially greater than that of its parent, thus giving the flowers of my new variety a longer life in respect to both color and form; the bud form of my new variety is only slightly urn-shaped, and is more nearly long-pointed than the buds of "Soeur Therese" which have a vary pronounced urn shape; the flowers of my new variety have many more petals than the parent, numbering from 37 to 45 petals, whereas the flowers of "Soeur Therese" are more appropriately classified as semi-double and have not more than 16 to 20 petals; the plant of my new variety is more compact and more thickly branched than the plants of "Soeur Therese" which are inclined to be rangy and tall in their habit of growth; and the buds and flowers of my new variety are more nearly a pure yellow color than those of the parent variety which frequently show considerable overlay of red pigment, especially in the bud.

In comparison with its pollen parent "Golden

Dawn," my new variety is particularly distinguished from this parent by the fact that the color of the buds and open flowers of my new variety are definitely deeper in their shade of yellow than that found in the buds and flowers of this parent; and the foliage of my new variety is a lighter shade of green and is somewhat smaller than that of "Golden Dawn." Still further, the form of the buds of this parent is usually short-pointed or ovoid, whereas the form of the buds of my new variety is distinctly long-pointed to urn-shaped.

Asexual reproduction of my new variety by budding at Ontario, California, shows that the foregoing characteristics and distinctions come true to form and are established and transmitted through succeeding propagations.

The accompanying drawing shows specimens of my new variety, with the flowers and foliage in different stages of development and depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated "Wilson") and Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Soeur Therese."

*Pollen parent.*—"Golden Dawn."

Propagation: Holds its distinguishing characteristics through succeeding propagations by budding.

*Flower*

Locality where grown and observed: Ontario, California.

Flowers borne: Usually singly, but sometimes 2 to 3 to stem; on normal to strong, medium to long stems.

Quantity of bloom: Free, outdoors.

Continuity: Nearly continuous during growing season.

Fragrance: Penetrating; tea to spicy.

Bud:

*Peduncle.*—Average length; average caliper; erect; smooth; numerous gland-tipped cilia; some soft prickles. Color—between Calliste Green, Plate VI (Ridgway), and Parrot Green, Plate VI (Ridgway), with slight shading of near Corinthian Purple, Plate XXXVIII (Ridgway), and Neutral Red, Plate XXXVIII (Ridway), on the side exposed to the sun.

*Before calyx breaks.*—Size—medium. Form—medium length; ovoid; usually with foliaceous appendages; few hairs; few gland-tipped cilia on the surface of the bud; usually with fairly stout, much-cut bristle-like foliaceous parts extending beyond the tip of the bud equal to ¼ or slightly more of its length.

*As calyx breaks.*—Color—near Lemon Yellow, Plate 4/1, page 4 (Wilson) and Buttercup Yellow, Plate 5, page 5 (Wilson); sometimes shaded, usually along margin of petals, with near Vermilion, Plate 18/2, page 18 (Wilson).

*Sepals.*—With fine, wooly tomentum; margins sometimes lined with wooly tomentum; others lined with gland-tipped cilia, stipitate glands and hairs.

*As first petal opens.*—Size—Average. Form—medium length to long; pointed to urn-shaped. Color—outside: near Lemon Yellow, Plate 4/1, page 4 (Wilson); sometimes dotted and shaded slightly with near Vermilion, Plate 18/2, page 18 (Wilson); inside: near Lemon Yellow, Plate 4/1, page 4 (Wilson); sometimes dotted and shaded slightly with near Vermilion, Plate 18/2, page 18 (Wilson).

*Opening.*—Opens up well; is not retarded from opening by cold, hot, dry or wet weather.

Bloom:

*Size, when fully open.*—Average; from 3½ to 4¼ inches.

*Petalage.*—Double; from 37 to 45 petals, plus 5 to 8 petaloids; arranged regularly.

*Form.*—High-centered at first; becoming open later; petals being at first flat-cupped, with lateral margins of upper portion reflexed for ¾ of length of petal; apex rarely reflexed; becoming flat later at maturity, with lateral margins usually reflexed for entire length of petal.

Petals:

*Texture.*—Medium to thick; leathery; with inside velvety and outside satiny.

*Shape.*—Outside—obovate; with apex usually flat. Intermediate—obovate; with apex rounded to flat; sometimes with 1 or 2 notches. Inside—narrowly obovate; somewhat irregular; with apex rounded; sometimes with 1 or 2 notches.

This description of a newly opened flower was made from a rose grown outdoors in the month of October, at Ontario, California:

*Color.*—Outside petal—outside surface: between Lemon Yellow, Plate 4/1, page 4 (Wilson) and Lemon Yellow, Plate 4/2, page 4 (Wilson); sometimes slightly marked with near Vermilion, Plate 18/2, page 18 (Wilson); inside surface—between Lemon Yellow, Plate 4, page 4 (Wilson) and Lemon Yellow, Plate 4/1, page 4 (Wilson); sometimes slightly marked with near Vermilion, Plate 18/2, page 18 (Wilson). Intermediate petal—outside surface: between Lemon Yellow, Plate 4/1, page 4 (Wilson) and Lemon Yellow, Plate 4/2, page 4 (Wilson); sometimes slightly marked with near Vermilion, Plate 18/2, page 18 (Wilson); inside surface: between Lemon Yellow, Plate 4, page 4 (Wilson) and Lemon Yellow, Plate 4/1, page 4 (Wilson); sometimes slightly marked with near Vermilion, Plate 18/2, page 18 (Wilson). Inner petal—outside surface: between Lemon Yellow, Plate 4/1, page 4 (Wilson) and Lemon Yellow, Plate 4/2, page 4 (Wilson); sometimes slightly marked with near Vermilion, Plate 18/2, page 18 (Wilson); inside surface: between Lemon Yellow, Plate 4, page 4 (Wilson) and Lemon Yellow, Plate 4/1, page 4 (Wilson).

This description was made from a rose that was open for three days outdoors during the month of October, at Ontario, California:

*Color.*—Outside petal—outside surface: near Canary Yellow, Plate 2/3, page 2 (Wilson); inside surface: between Canary Yellow, Plate 2/2, page 2 (Wilson) and Canary Yellow, Plate 2/3, page 2 (Wilson). Inside petal—outside surface: near Canary Yellow, Plate 2/3, page 2 (Wilson); inside surface: between Canary Yellow, Plate 2/2, page 2 (Wilson) and Canary Yellow, Plate 2/3, page 2 (Wilson).

*General color effect.*—Newly opened flower—near Lemon Yellow, Plate 4/1, page 4 (Wilson); sometimes slightly marked with near Vermilion, Plate 18, page 18 (Wilson). Three days open—near Canary Yellow, Plate 2/2, page 2 (Wilson).

*Behavior.*—Drop off cleanly, except for occasional petaloids which persist; not ordinarily affected by cold, hot, wet or dry weather.

*Flower longevity.*—On bush in garden—3 days in October. Cut roses grown outdoors and kept at living-room temperatures—3 to 4 days in October.

*Reproductive organs*

Stamens: Average number to many; arranged regularly about pistils.

Flaments: Most with anthers.

*Lengths.*—Short to medium; 3 to 7 mm. long.

*Color.*—Near Fire Red, Plate 15/1, page 15 (Wilson) to Poppy Red, Plate 16/1, page 16 (Wilson).

Anthers: Medium size; all open approximately at once. Color—upper side: margins near Saffron Yellow, Plate 7, page 7 (Wilson) and near Fire Red, Plate 15/1, page 15 (Wilson); remainder near Lemon Yellow, Plate 4/2, page 4 (Wilson); under side: margins near Saffron Yellow, Plate 7, page 7 (Wilson); remainder near Lemon Yellow, Plate 4/2, page 4 (Wilson).

Pollen: Moderate abundance. Color—near Indian Yellow, Plate 6/2, page 6 (Wilson).

Pistils: Average number to many; approximately 70 in number.

Styles: Even; average length; average caliper; bunched; 6 to 8 mm. long. Color—near Mandarin Red, Plate 17/1, page 17 (Wilson) for about ⅓ of its length near stigma; remainder between Uranium Green, Plate 63/2, page 63 Wilson) and Dresden Yellow, Plate 64, page 64 (Wilson).

Stigma: Color—near Lemon Yellow, Plate 4/2, page 4 (Wilson).

Ovaries: Usually all protruding from calyx.

Hips: Rarely sets hips.

Sepals: Permanent; medium-length; recurved. Color—inside: near Biscay Green, Plate XVII (Ridgway), modified by covering of white tomentum; outside: between Calliste Green, Plate VI (Ridgway) and Parrot Green, Plate VI (Ridgway).

Seeds: Rarely sets seeds.

*Plant*

Foliage:

*Leaves.*—Compound of usually 5 to 7 leaflets; normal abundance; medium size; somewhat leathery.

*Leaflets.*—Ovoid; apex acute; base round; margin doubly serrate.

*Color.*—Mature — upper surface: between Biscay Green, Plate XVII (Ridgway) and Light Elm Green, Plate XVII (Ridgway); under surface: near Courge Green, Plate XVII (Ridgway). Young—upper surface: near Oil Green, Plate V (Ridgway), with near Neutral Red, Plate XXXVIII (Ridgway); under surface: near Mineral Red, Plate. XXVII (Ridgway).

*Rachis (the supporting stem of the compound leaf).*—Light to average size; upper side grooved, with many stipitate glands on edges; under side prickly.

*Stipules.*—Medium length to long; medium width; with long points turning out at an angle of less than 45° and recurved somewhat toward the stem.

*Disease resistance.*—Better than average resistance to mildew as determined by comparison with other varieties grown under comparable conditions at Ontario, California.

Growth:

*Habit.*—Bushy; spreading; much-branched.

*Growth.*—Moderate.

*Canes.*—Medium caliper.

*Main stems.*—Color—between Yellowish Oil Green, Plate V (Ridgway) and Oil Green, Plate V (Ridgway). Large prickles—several to many; medium-length; almost straight; with medium-length, narrow base. Color—between Cinnamon-Brown, Plate XV (Ridgway) and Prout's Brown, Plate XV (Ridgway). Small prickles—none. Hairs—none.

*Branches.* — Color — near Courge Green, Plate XVII (Ridgway). Large prickles—several; medium-length; almost straight; with medium-length, narrow base. Color — near Cinnamon-Brown, Plate XV (Ridgway). Small prickles—few. Color—near Cinnamon-Brown, Plate XV (Ridgway). Hairs—none.

*New shoots.*—Color — between Hydrangea Red, Plate XXVII (Ridgway) and Mineral Red, Plate XXVII (Ridgway). Large prickles—several; medium-length; almost straight; with medium-length, narrow base. Color—near Mineral Red, Plate XXVII (Ridgway). Small prickles—very few. Color—near Mineral Red, Plate XXVII (Ridgway). Hairs—none.

I claim:

A new and distinct variety of rose plant of the hybrid tea class, substantially as herein shown and described, characterized particularly as to novelty by its bushy, compact, much-branched and slightly spreading habit of growth, by the long-pointed and slightly urn-shaped form of its buds, by the double petalage and superior petal substance of its flowers, by the rich yellow color of its buds and flowers, and by the prolonged retention of the coloring, with attending long life of the flowers in respect to both their color and form.

HERBERT C. SWIM.

No references cited.